United States Patent [19]

Owens et al.

[11] Patent Number: 5,641,065
[45] Date of Patent: Jun. 24, 1997

[54] MEDICAL INSTRUMENT SOAKING, TRANSPORTING AND STORAGE CONTAINER

[75] Inventors: Daniel Owens; Daniel L. Sands, both of Silver Lake; Ron Vanderpool, Warsaw, all of Ind.

[73] Assignee: Paragon Group of Plastics Companies, Inc., Warsaw, Ind.

[21] Appl. No.: 493,797

[22] Filed: Jun. 22, 1995

[51] Int. Cl.[6] .............. B65D 45/20; A61L 2/06; A61L 2/26
[52] U.S. Cl. .......... 206/370; 206/363; 220/324; 422/300; 422/310
[58] Field of Search ............... 422/300, 297, 422/310; 220/308, 310, 324, 357, 358; 206/363, 370

[56] References Cited

U.S. PATENT DOCUMENTS

| 2,510,643 | 6/1950 | Long | 220/324 X |
|---|---|---|---|
| 3,464,579 | 9/1969 | Asenbauer | 220/324 X |
| 4,915,913 | 4/1990 | William et al. | 422/297 X |
| 4,919,888 | 4/1990 | Spence | 422/300 X |
| 4,971,774 | 11/1990 | Schwanke et al. | 422/310 |
| 5,372,787 | 12/1994 | Ritter | 422/300 X |

FOREIGN PATENT DOCUMENTS

| 437216 | 12/1911 | France | 220/324 |
|---|---|---|---|
| 1368150 | 12/1964 | France | 220/324 |

*Primary Examiner*—Bryon P. Gehman
*Attorney, Agent, or Firm*—Baker & Daniels

[57] ABSTRACT

A medical instrument soaking, transport and storage container intended for receiving surgical instruments and containing a cleaning solution or disinfectant for cleaning the instruments. A lid mounts on the bowl for transport of the instruments to a cleaning/decontamination area of a hospital. The lid portion carries a projecting seal that is received in a circumferentially extending groove in an outwardly extending rim portion of the bowl. Accordingly, sealing is effected between the lid and the bowl. A pivoting clasp is mounted on each side of the lid for engagement with the corresponding portion of the bowl, and therefore secures the lid on the bowl for transport.

6 Claims, 3 Drawing Sheets

5,641,065

MEDICAL INSTRUMENT SOAKING, TRANSPORTING AND STORAGE CONTAINER

This invention relates to a container for storing, transporting and soaking surgical instruments after surgery.

BACKGROUND OF THE INVENTION

After surgical instruments are used in surgery, the instruments are placed in a soaking or disinfecting solution within a container to loosen the blood and tissue left on the instruments after surgery. After surgery is complete, the container containing the instruments is transported to the decontamination and cleaning area of the hospital. Existing medical instruments soaking and transfer containers are usually left open; accordingly, the contaminated cleaning solution cannot be readily contained. Of course, regulations now require special care be given to medical waste products. Since a wide variety of cleaning solutions must be used, special materials, generally polypropylene, must be used in medical containers.

SUMMARY OF THE INVENTION

The present invention provides a medical container having a lid and a seal. When the lid is fastened to the container, the seal engages the rim of the container thereby sealing the container for transport to the contamination and cleaning area of the hospital. The materials used to make the container are sufficiently inert that any necessary cleaning agents can be used, and these materials are incompatible with adhesives. Accordingly, the seal cannot be attached to the lid in the usual manner by using adhesives as adhesives are incompatible with materials such as polypropylene from which the container lids is made. Accordingly, the lid is drawn around the seal, so that the seal is secured to the lid thereby. Additional sealing members are used to retain pivot pins on which the closing latches are mounted, thereby not only retaining the pivot pins of the lid but assuring the seal between lid and container. Furthermore, the lid is designed so that the containers may stack upon one another, with a rim on the lid which retains the seal acting as a barrier to prevent the stacked container from sliding off of the lower container. The seal is received in a groove in the rim of the container and includes a notch in the lower end of the seal to thereby permit the seal to flex and inherently engage the side walls of the groove. Of course, the container can be made in various sizes and configurations to allow use of many different instruments that are normally soaked in cleaning solution, some containers may be entirely dry or provided with a dry area since some instruments are sensitive to moisture.

BRIEF DESCRIPTION OF THE DRAWING

These and other advantages of the present invention become apparent from the following description with reference to the accompanying drawings, in which.

DETAILED DESCRIPTION

Figure 1:
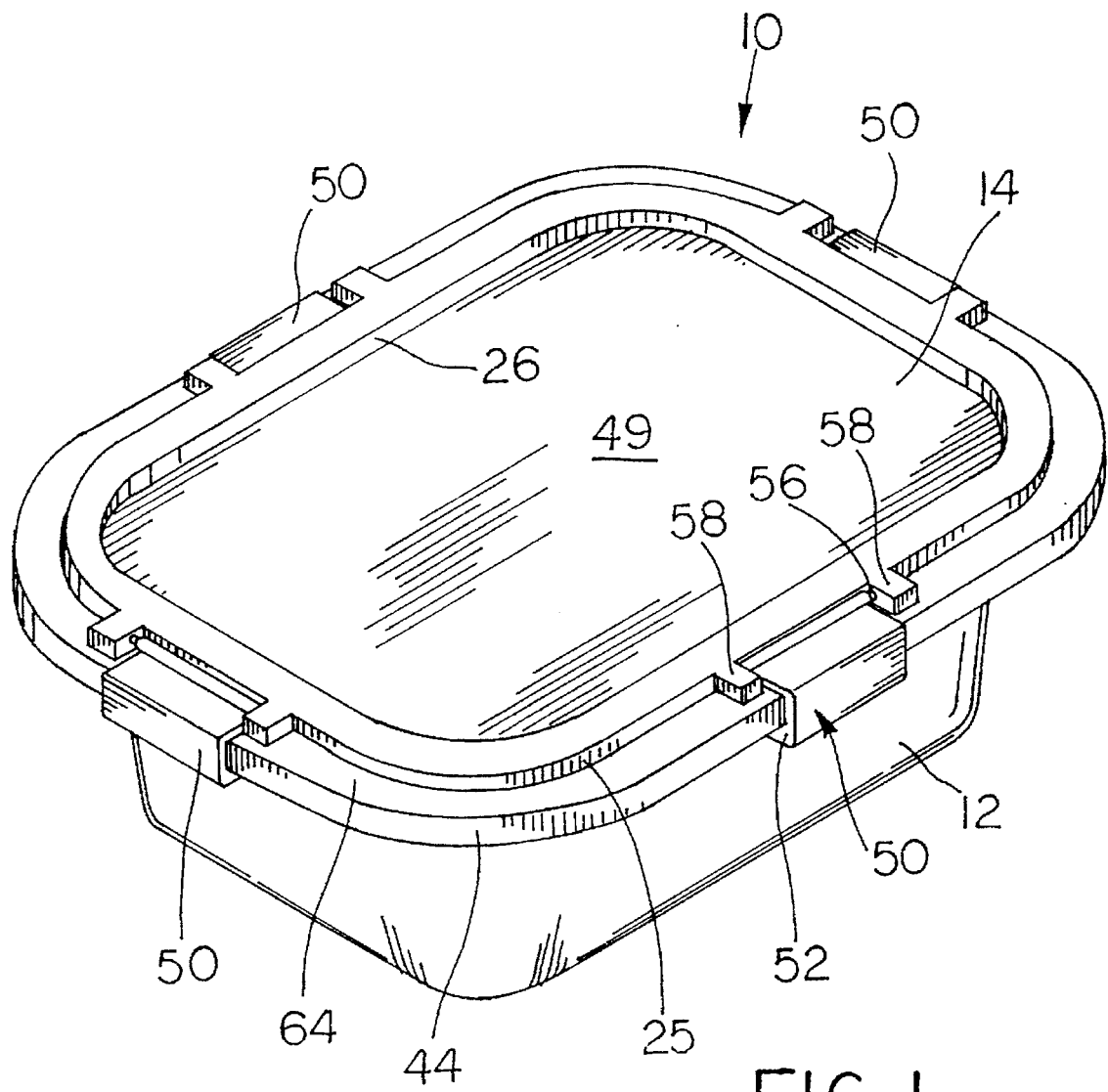
FIG. 1 is a perspective view of a storage container made according to the teachings of the present invention.
Figure 2:
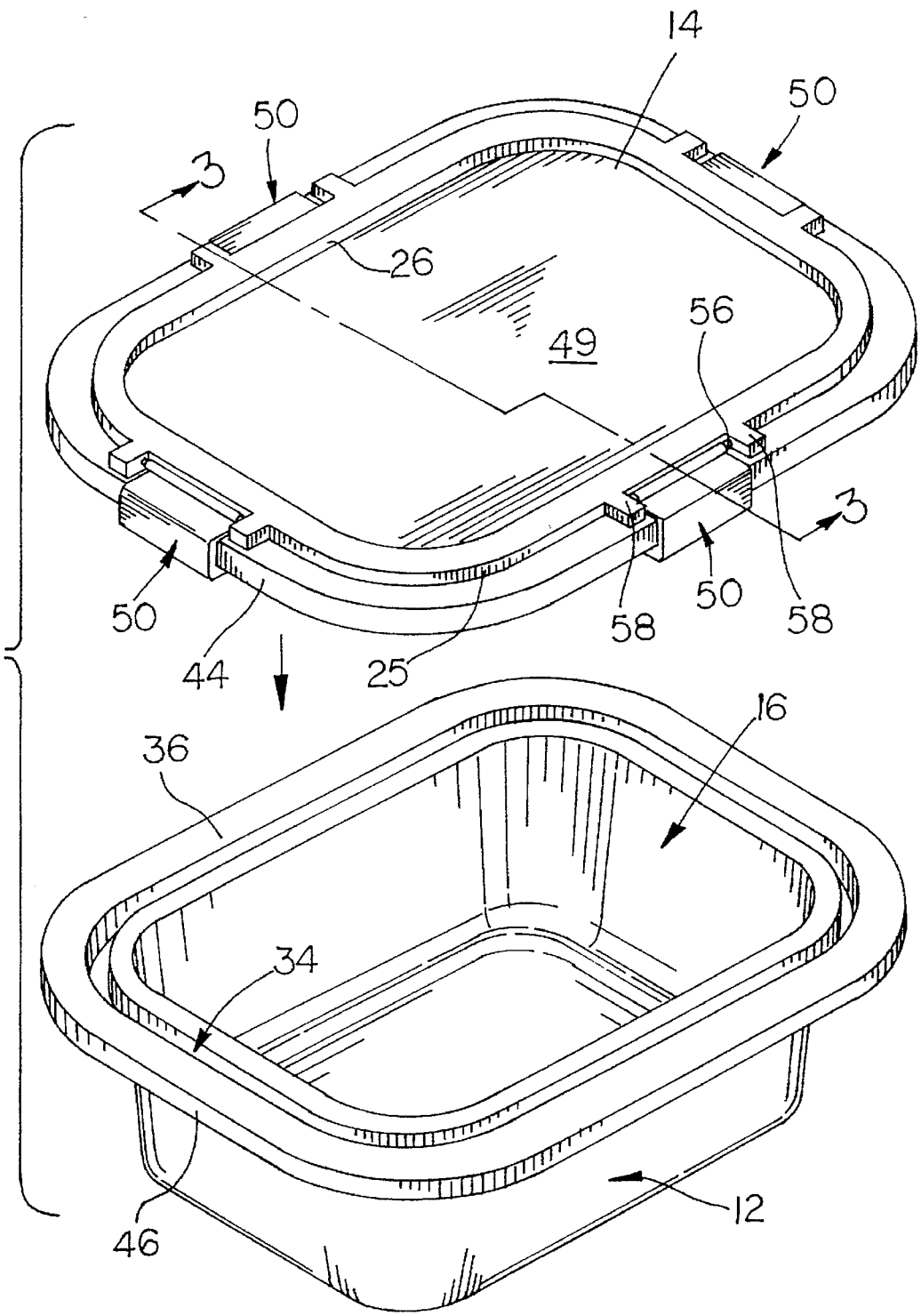
FIG. 2 is an exploded view of the perspective medical instrument soaking and storage container illustrated in FIG. 1, the lid portion being shown removed off of the bowl portion of the container.
Figure 3:
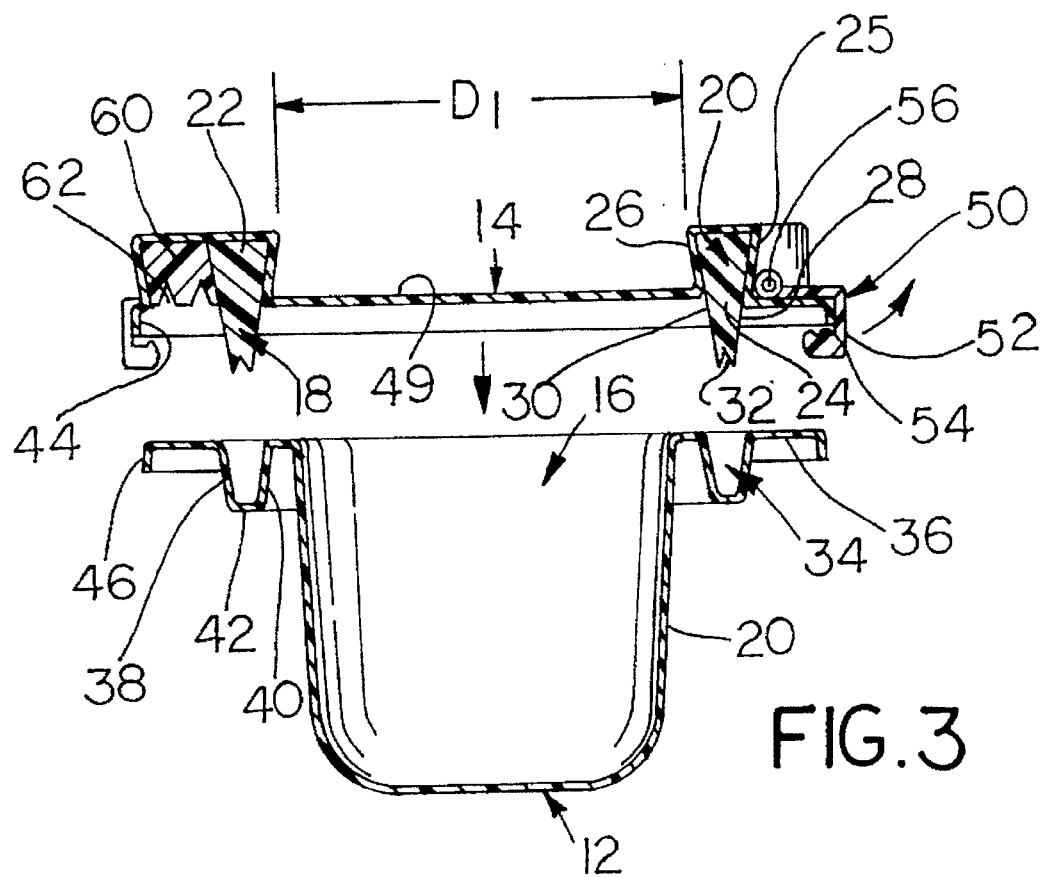
FIG. 3 is a view taken substantially along line 3—3 of FIG. 2.
Figure 4:
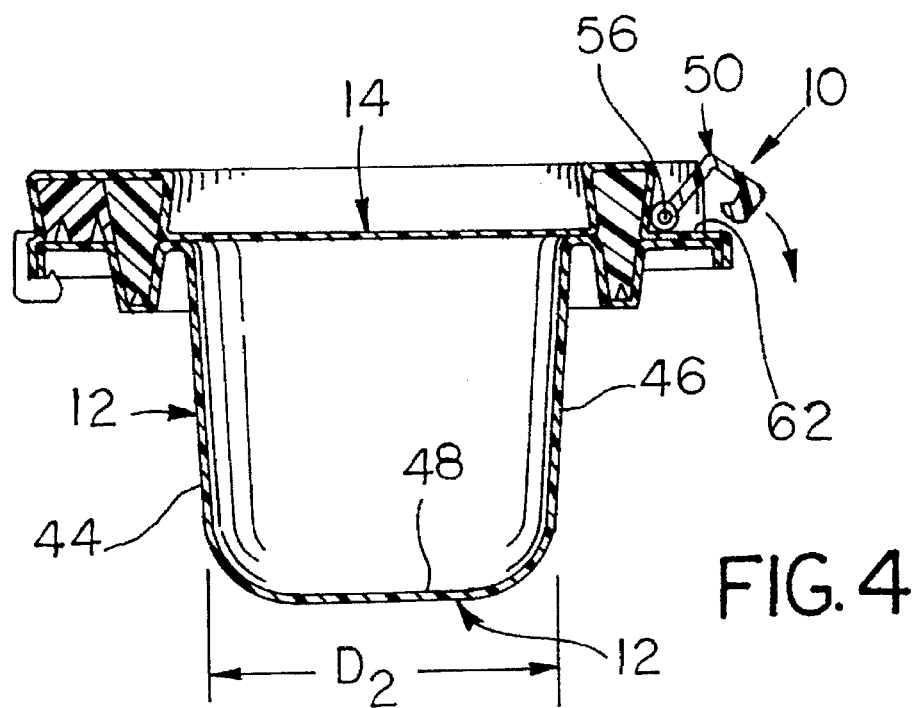
FIG. 4 is a view similar to FIG. 3 but illustrating the container with the lid portion on the bowl portion of the container.

Referring now to the drawings, a medical instrument storing and soaking container generally indicated by the numeral 10 includes a bowl portion 12 and a lid portion 14. The bowl portion 12 includes an opening 16 which receives the medical instruments and the necessary cleaning and soaking fluid and the opening 16 being closed by the lid 14 when the lid is installed thereon as shown in FIGS. 1 and 4 to assure containment of the medical instruments and cleaning fluid during transport. The lid portion 14 carries a circumferentially extending resilient seal 18 in a circumferentially extending groove 20 defined in the lid portion 14 which circumscribes the opening 16 when the lid 14 is installed on the bowl portion 20. The seal 18 includes a retaining portion 22 within the groove 20 and a projecting portion 24 which projects from the groove 20. The retaining section 22 has a differential cross sectional area tapering from a maximum cross sectional area near the bottom of the groove to a minimum cross sectional area. The groove is a pair of inwardly tapering sidewalls 25, 26 that engage the tapering sides 28, 30 of the seal 18. When the lid 14 is manufactured from a flat sheet of polypropylene material, the seal 18 is formed and placed in the mold, and then the sheet is drawn around the retaining portion of the groove by vacuum forming. Accordingly, the inwardly tapering sides 25, 26 of the groove, due to their engagement with the tapering sides 28, 30 of the seal, firmly hold the seal within the groove, such that no adhesives or other fasteners are necessary to secure the seal 18 to the lid portion 14. This is important because the sterilization container 10 must be made of a highly chemical resistant plastic, such as polypropylene, in order to withstand the chemical cleaning solutions that are used to clean clinical instruments. Such highly chemical resistant materials are incompatible with most known economical adhesives, so that adhesives are not available to secure the seal 18 to the lid portion 14. A circumferentially extending notch or groove 32 is provided in the portion of the seal 18 connecting the sides 28, 30 at the lowermost portion thereof viewing FIGS. 3 and 4.

The projecting portion 24 of seal 18 is received in a circumferentially extending groove 34 in the bowl portion 12 when the lid portion 14 is mounted on the bowl portion 12 as illustrated in FIGS. 1 and 4. Circumferentially extending groove 34 is formed in a circumferentially extending rim 36 which projects outwardly from the bowl defined in bowl portion 12. The groove 34 is formed by tapering sides 38, 40 and connecting portion 42 which extends between sides 38, 40. When the lid portion 14 is installed on the bowl portion 12, the projecting portion of the seal 18 is received within the groove 30, the sides 30, 28 flexing relative to one another such that the resiliency of the seal yieldably urges the sides 30, 28 into sealing engagement with the walls 38, 40 of the groove 34. The notch 32 allows additional flexure between the sides 28, 30 over that which otherwise would be the case to assure that a tight sealing engagement is maintained between the projecting portion 24 seal 18 and the groove 34.

A downwardly projecting, circumferentially extending, terminal portion 44 of the lid portion 14 slidably engages downwardly projecting circumferentially extending portion 46 extending from the rim 36, when the lid portion is installed on the bowl portion, as illustrated in FIG. 4. It will be noted that the minimum distance D1 between the sides of the groove 20 is just slightly less than the minimum distance D2 between the sides 44, 46 of the bowl portion 12. Accordingly, multiple containers 10 may be stacked upon one another when the lid is mounted on the bowl with relative sliding movement of one container relative to the other being inhibited by sidewall 26 when the bottom 48 of the bowl portion 12 is resting on the relatively flat upper surface 49 of the lid portion 14. Accordingly, transport of multiple containers of instruments between the operating room and the decontamination and cleaning area of the hospital is facilitated.

The lid portion 14 is secured to bowl portion 12 by latching members generally indicated by the numeral 50. One of the latching members 50 is mounted on each side of the lid portion 14, and, since all of the latch members 50 are identical, only one will be described in detail. Each of the latch member 50 includes a clasp portion 52 terminating in an upwardly extending projection 54, viewing FIGS. 3 and 4. Latch members 50 are pivotly mounted on the lid portion 14 by a pivot pin 56, which permits pivoting of the each latch member 50 upwardly as indicated by the arrow in FIG. 3, and downwardly as indicated by the arrow in FIG. 4. Opposite ends of the pivot pin 56 extend into corresponding extensions 58 which project from the wall 25 of the groove 20 defined in the lid portion 14. Resilient members 60, which may be made of the same resilient material as is the seal 18, are molded within the extensions 58 by drawing material around them as discussed here above with respect to the seal 18 when the lid is manufactured. Accordingly, the resilient members 60 not only retain the pivot pin 56 and therefore the entire latch mechanism in place, but also insures against leakage around the pivot pin 56. The contour 62 at the bottom edge of the resilient member 60 (view in FIG. 3) is provided to locate the member 60 within the mold (not shown) when the lid is manufactured and serves no other purpose.

Accordingly, during surgery, a cleaning solution is dispensed into the bowl portion 12. As instruments are used during surgery, they are deposited in the cleaning solution contained within the bowl after they are used. When surgery is complete, said portion is installed on the bowl portion 12 by installing the projecting portion 24 of the circumferentially seal 18 into the groove 34 defined in rim 16. At the same time, downwardly projecting portion 44 of lid portion 14 will fit over the downwardly projecting portion 46 of rim 36 of the bowl portion 12. Accordingly, substantially flat portion 64 of the lid portion 14 will rest directly upon the rim 36 of bowl portion 12. The clasp 50 can then be rotated downwardly as indicated by the arrow such that the clasp portion 52 will rotate around the downwardly projection portions 44, 46 to thereby cause the projecting portion 54 to latch against the projection of 46, thereby firmly securing the lid portion 14 upon the bowl portion 12. Additional containers 10 can then be stacked upon one another, with the bottom 48 of bowl portion 16 of successive containers resting upon the substantially flat surface 50 of lid portion 14, relative sliding movement between the containers stacked upon one another being restrained by the edge 26.

We claim:

1. Medical instrument container comprising a bowl member having an opening for receiving instruments, a lid member for closing the opening of said bowl member, and latch means for securing the lid member to the bowl member, one of said members carrying a circumferentially extending seal circumscribing said opening in the bowl member when the lid member is installed on the bowl member to close said opening, said one member including a circumferentially extending groove receiving said seal, said seal having a circumferentially extending retaining portion within said groove and a circumferentially extending projecting portion extending from the retaining portion and projecting out of said groove, the other member having a circumferentially extending groove circumscribing the opening in said bowl member and receiving the projecting portion of said seal when the lid member is secured to the bowl member, said retaining portion and said groove in said one member having differential cooperating cross sectional areas whereby said seal is retained in said groove in said one member by said differential cooperating cross sectional areas.

2. Medical instrument container as claimed in claim 1, wherein said groove in said one member includes inwardly tapering side edges defining the differential cross sectional area of the groove in said one portion, said seal having tapering side edges defining the differential cross sectional area of the seal, the sides of the groove in the one portion engaging the sides of the seal to maintain the seal in the groove in said one portion.

3. Medical instrument container comprising a bowl member having an opening for receiving instruments, a lid member for closing the opening of said bowl member, and latch means for securing the lid member to the bowl member, one of said members carrying a circumferentially extending seal circumscribing said opening in the bowl member when the lid member is installed on the bowl member to close said opening, said one member including a circumferentially extending groove receiving said seal, said seal having a circumferentially extending retaining portion within said groove and a circumferentially extending projecting portion extending from the retaining portion and projecting out of said groove, the other member having a circumferentially extending groove circumscribing the opening in said bowl member and receiving the projecting portion of said seal when the lid member is installed on the bowl member, wherein said bowl member includes a circumferentially extending rim projecting outwardly from said opening, one of said grooves being defined in said rim, the other groove registering with said rim, the groove in the lid member being defined within a projecting rim circumscribing a substantially flat area on the lid member, said seal including a pair of opposite side edges and a connecting edge connecting said side edges, said connecting edge including a notch to permit said side edges to flex relative to the groove in the other member to assure sealing contact between said side edges of the seal and said groove in the other member.

4. Medical instrument container as claimed in claim 3, wherein said one portion includes a circumferentially extending rim projecting outwardly from said opening, the groove in said other portion being defined on said rim and receiving the projecting portion of the seal when the lid portion is installed on the bowl portion, said groove in said other portion having inwardly tapering edges engaging the side edges of the seal, said notch in said connecting edge of the seal permitting the side edges of the seal to yieldably engage the inwardly tapering edges.

5. Medical instrument container as claimed in claim 4, wherein said latch means includes a latch member pivotally connected to said lid portion by a pivot pin, said one groove being defined in said lid portion and having extensions receiving opposite ends of said pivot pin, and an extension seal within each of said extensions engaging said opposite ends of the pivot pin to retain the pivot pin in said extensions and to seal around said pivot pin.

6. Medical instrument container comprising a bowl member having an opening for receiving instruments, a lid member for closing the opening of said bowl member, and latch means for securing the lid member to the bowl member, one of said members carrying a circumferentially extending seal circumscribing said opening in the bowl member when the lid member is installed on the bowl member to close said opening, said one member including a circumferentially extending groove receiving said seal, the other member having a circumferentially extending groove circumscribing the opening in said bowl member and receiving a projecting portion of said seal when the lid member is secured to the bowl member, said bowl member including a circumferentially extending rim projecting outwardly from said opening, one of said grooves being defined in said rim, the other groove registering with said rim, the groove in the lid member being defined within a projecting rim circumscribing a substantially flat area on the lid member, said seal including a pair of opposite side edges and a connecting edge connecting said side edges, said connecting edge including a notch to permit said side edges to flex relative to the groove in the other member to assure sealing contact between said side edges of the seal and said groove in the other member.

\* \* \* \* \*